United States Patent [19]
Reed et al.

[11] Patent Number: 5,686,595
[45] Date of Patent: Nov. 11, 1997

[54] BCL-2-ASSOCIATED PROTEINS

[75] Inventors: John C. Reed, Carlsbad; Shinichi Takayama; Takaaki Sato, both of San Diego, all of Calif.

[73] Assignee: La Jolla Cancer Research Foundation, La Jolla, Calif.

[21] Appl. No.: 461,359

[22] Filed: Jun. 5, 1995

Related U.S. Application Data

[62] Division of Ser. No. 152,405, Nov. 12, 1993, Pat. No. 5,539,094.

[51] Int. Cl.$^6$ .......................... C12N 15/00; C07H 21/04; C07H 21/02
[52] U.S. Cl. ...................... 536/23.5; 536/23.1; 536/24.5; 435/172.3
[58] Field of Search ............................. 536/23.5; 514/44

[56] References Cited

PUBLICATIONS

Gura, Antisense has growing pains, Science 270:575–577, Oct. 1995.
Hodgson, The vector void in Gene Therapy, Biotechnology, 13:222–227, Mar. 1995.
Stein et al, Antisense Oligodeoxynucleotides, Current Opinions in Oncology, 6:67–594, 1994.
Milligan et al, Current Concepts in Antisense Drug Design, Journal of Medicinal Chemistry, 36:(14) 1925–1937, Jul. 1993.
Hanada, Motoi et al., "Regulation of Bcl–2 Oncoprotein Levels with Differentiation of Human Neuroblastoma Cells." *Cancer Res.*53:4978–4986 (1993).
Tanaka, Shigeki et al, "Structure–Function Analysis of the Bcl–2 Oncoprotein." *J. Biol. Chem.*268:10920–10926 (1993).
Hockenbery, D. et al., "Bcl–2 is an Inner Mitochondrial Membrane Protein that Blocks Programmed Cell Death." *Nature* 348:334–336 (1990).
Boise, Lawrence H. "bcl–x, a bcl–2–Related Gene that Functions as a Dominant Regulator of Apoptotic Cell Death." *Cell* 74:597–608 (1993).
Miyashita, T. and Reed, J.C. "Bcl–2 Oncoprotein Blocks Chemotherapy–Induced Apoptosis in a Human Leukemia Cell Line." *Blood* 81:151–157 (1993).
Vaux, D.L., "Toward an Understanding of the Molecular Mechanisms of Physiological Cell Death." *Proc. Natl. Acad. Sci. USA*. 90:786–789 (1993).
Vaux, D. et al., "Bcl–2 Gene Promotes Haemopoietic Cell Survival and Cooperated with c–myc to Immortalize Pre–B Cells." *Nature* 335:440–442 (1988).
Kocache, Malda M. and Pearson, Gary R. "Protein Kinase Activity Associated with a Cell Cycle Regulated, Membrane–Bound Epstein–Barr Virus Induced Early Antigen." *Intervirology* 31:1–13 (1990).
Oltvai, Zoltán N. et al., "Bcl–2 Heterodimerizes In Vivo with a Conserved Homolog, Bax, that Accelerates Programed Cell Death." *Cell* 74:609–619 (1993).

Nunez, Gabriel et al., "Deregulated Bcl–2 Gene Expression Selectively Prolongs Survival of Growth Factor–Deprived Hemopoietic Cell Lines." *J. Immunl.* 144:3602–3610 (1990).
Garcia, Irene et al., "Prevention of Programmed Cell Death of Sympathetic Neurons by the Bcl–2 Proto–Oncogene." *Science* 258:302–304 (1992).
Bissonnette, Reid P et al., "Apoptotic Cell Death Induced by c–myc is Inhibited by Bcl–2." *Nature* 359:552–554 (1992).
Fanidi, Abdallah et al., "Cooperative Interaction Between c–myc and bcl–2 Proto–Oncogenes." *Nature* 359:554–556 (1992).
Vaux, David L. et al., "Prevention of Programmed Cell Death in *Caenorhabditis elegans* by Human bcl–2." *Science* 258:195–197 (1992).
Alnemri Emad S. et al., "Overexpressed Full–Length Human BCL2 Extends the Survival of Baculovirus–infected Sf9 Insect Cells." *Proc. Natl. Acad. Sci. USA* 89:7295–7299 (1992).
Siegel, Richard M. et al., "Inhibition of Thymoyte Apoptosis and Negative Antigenic Selection in bcl–2 Transgenic Mice." *Proc. Natl. Acad. Sci. USA* 89:7003–7007 (1992).
Sentman, Charles L. et al., "bcl–2 Inhibits Multiple Forms of Apoptosis but Not Negative Selection in Thymocytes." *Cell* 67:879–888 (1991).
Strasser, Andreas et al., "bcl–2 Transgene Inhibits T Cell Death and Perturbs Thymic Self–Censorship." *Cell* 67:889–899 (1991).
McDonnell, Timothy J. et al., "bcl–2–Immunoglobulin Transgenic Mice Demonstrate Extended B Cell Survival and Follicular Lymphoproliferation." *Cell* 57:78–88 (1989).
Wagner Andrew J. et al., "Myc–Mediated Apoptosis is Blocked by Ectopic Expression of Bcl–2." *Mole. Cell Biol.* 13(4) 2432–2440 (1993).
Fernandez–Sarabia, Maria J. and Bischoff, James R. "Bcl–2 Associates with the ras–Related Protein R–ras p23." *Nature* 366:274–275 (1993).
Lee, Sooja et al., "Apoptosis and Signal Transduction: Clues to a Molecular Mechanism." *Current Opinion Cell Biol.* 5:286–291 (1993).
Donahue et al JE01 176: 1125, 1992.
Coughler in few Scientist, pp. 14 & 15, 25 Nov. 1995.
Marshall et al Science 269: 1050, 1995.
Orkin et al "Report & Recommendations of the Panel to Assess the NIH Investment in Research . . .", Dec., 7, 1995.
Miller et al Parasitology Today 10(3): 92, 1994.

*Primary Examiner*—Suzanne E. Ziska

[57] ABSTRACT

The present invention provides nucleotide sequences encoding proteins and fragments thereof that bind to Bcl-2-related proteins. The invention also provides a Bcl-2-associated protein (BAP) such as Bcl-2-associated protein-1 (BAP-1), which binds to Bcl-2. The invention also provides antibodies that specifically bind to a BAP. The invention further provides methods for detecting agents such as drugs that alter the binding of a BAP such as BAP-1 or Raf-related protein with a Bcl-2-related protein and methods for detecting agents that induce dissociation of a bound complex formed by the association of a BAP and a Bcl-2-related protein. The invention further provides methods for modulating the activity of a Bcl-2-related protein in a cell by introducing into the cell a nucleic acid encoding a BAP or by introducing into the cell an antisense nucleotide sequence, which is complementary to a region of a gene encoding a BAP.

2 Claims, 5 Drawing Sheets

|          10         20         30         40         50    |      |
| 1234567890 1234567890 1234567890 1234567890 1234567890 |      |
| CGCCTGCAAG CCGCGGGTGA AGAAGAAAGT CCGGCCCCGC TCTTCTCAGA | 50   |
| GCGAGAAGGT AGGGAGCAGC AGCAGGGAGT TGACTAGAAG TAAGAAAGTG | 100  |
| ACCCGTAGCA AGAACGTGAC CGGGACCCAG GTAGAGGAGG TGACCAAGAT | 150  |
| CGAGGAGGCG ACCCAAACCG AGGAAGTAAC TGTGGCAGAA GAGGTGACCC | 200  |
| AGACCGACAA CATGGCCAAG ACCGAGGAGA TGGTCCAGAC GGAGGAAATG | 250  |
| GAAACACCCA GACTCAGCGT GATCGTCACC CACAGCAATG AGAGGTATGA | 300  |
| CCTTCTTGTT ACCCCACAGC AAGGTAACAG TGAGCCAGTT GTCCAAGACT | 350  |
| TGGCTCAGCT TGTTGAAGAG GCCACAGGAG TTCCACTACC TTTTCAGAAG | 400  |
| CTCATATTTA AGGGAAAATC TCTGAAAGAA ATGGAAACAC CGTTGTCAGC | 450  |
| ACTTGGAATG CAAAATGGTT GCCGAGTCAT GTTAATTGGT GAAAAGAGCA | 500  |
| ATCCAGAAGA AGAGGTTGAG TTAAAGAAGC TGAAAGATTT GGAGGTATCT | 550  |
| GCAGAGAAGA TAGCTAACCA CCTGCAAGAA TTGAATAAAG AGCTTTCTGG | 600  |
| CATCCAGCAG GGTTTTCTGG CTAAGGAATT GCAAGCGGAG GCTCTCTGCA | 650  |
| AACTTGATAG GAAAGTAAAA GCAACAATTG AGCAATTCAT GAAGATCTTG | 700  |
| GAGGAGATTG ACACAATGGT CCTACCAGAA CAATTTAAAG ACAGCAGGCT | 750  |
| AAAAAGGAAG AATTTGGTGA AAAAGGTTCA GGTGTTCTTA GCAGAGTGTG | 800  |
| ACACAGTGGA GCAATACATC TGCCAAGAGA CAGAGCGGCT GCAGTCTACA | 850  |
| AACTTGGCCC TGGCTGAATG AAGTGCAGTG GAGAGTGGCT GTACTGGCCT | 900  |
| GAAGAGCAGC TTTACAGCCC TGCCCTCTCT GGAACAGAAG TCGCCTGTTT | 950  |
| CTCCATGGCT GCCAGGGCA ACTAGCCAAA TGTCAATTTC CCTGCTCCTC  | 1000 |
| CGTCGGTTCT CAATGAAAAA GTCCTGTCTT TGCAACCTGA AAAAAAAAAA | 1050 |
| AAAA                                                   | 1054 |

FIG. 1

|          10         20         30         40         50    |     |
| 1234567890 1234567890 1234567890 1234567890 1234567890 |     |
| MAKTEEMVQT EEMETPRLSV IVTHSNERYD LLVTPQQGNS EPVVQDLAQL | 50  |
| VEEATGVPLP FQKLIFKGKS LKEMETPLSA LGMQNGCRVM LIGEKSNPEE | 100 |
| EVELKKLKDL EVSAEKIANH LQELNKELSG IQQGFLAKEL QAEALCKLDR | 150 |
| KVKATIEQFM KILEEIDIMV LPEQFKDSRL KRKNLVKKVQ VFLAECDTVE | 200 |
| QYICQETERL QSTNLALAE                                   | 219 |

FIG. 2

|  | 10 | 20 | 30 | 40 | 50 |  |
|---|---|---|---|---|---|---|
|  | 1234567890 | 1234567890 | 1234567890 | 1234567890 | 1234567890 |  |
|  | CCTTCATGTT | ACCTCCCAGC | AGGGCAGCAG | TGAACCAGTT | GTCCAAGACC | 50 |
|  | TGGCCCAGGT | TGTTGAAGAG | GTCATAGGGG | TTCCACAGTC | TTTTCAGAAA | 100 |
|  | CTCATATTTA | AGGGAAAATC | TCTGAAGGAA | ATGGAAACAC | CGTTGTCAGC | 150 |
|  | ACTTGGAATA | CAAGATGGTT | GCCGGGTCAT | GTTAATTGGG | AAAAAGAACA | 200 |
|  | GTCCACAGGA | AGAGGTTGAA | CTAAAGAAGT | TGAAACATTT | GGAGAAGTCT | 250 |
|  | GTGGAGAAGA | TAGCTAACCA | GCTGGAAGAG | TTGAATAAAG | AGCTTACTGG | 300 |
|  | AATCCAGCAG | GGTTTTCTGC | CCAAGGATTT | GCAAGCTGAA | GCTCTCTGCA | 350 |
|  | AACTTGATAG | GAGAGTAAAA | GCCACAATAG | AGCAGTTTAT | GAAGATCTTG | 400 |
|  | GAGGAGATTC | ACACACTGAT | CCTGCCAGAA | AATTTCAAAG | ACAGTAGATT | 450 |
|  | GAAAAGGAAA | GGCTTGGTAA | AAAAGGTTCA | GGCATTCCTA | GCCGAGTGTG | 500 |
|  | ACACAGTGGA | GCAGAACATC | TGCCAGGAGA | CTGAGCGGCT | GCAGTCTACA | 550 |
|  | AACTTTGCCC | TGGCCGAGTG | AGGTGTAGCA | GAAAAGGCT | GTGCTGCCCT | 600 |
|  | GAAGAATGGC | GCCACCAGCT | CTGCCGTCTC | TGGATCGGAA | TTTACCTGAT | 650 |
|  | TTCTTCAGGG | CTGCTGGGGG | CAACTGGCCA | TTTGCCAATT | TTCCTACTCT | 700 |
|  | CACACTGGTT | CTCAATGAAA | AATAGTGTCT | TTG |  | 733 |

FIG. 3

|  | 10 | 20 | 30 | 40 | 50 |  |
|---|---|---|---|---|---|---|
|  | 1234567890 | 1234567890 | 1234567890 | 1234567890 | 1234567890 |  |
|  | LHVTSQQGSS | EPVVQDLAQV | VEEVIGVPQS | FQKLIFKGKS | LKEMETPLSA | 50 |
|  | LGIQDGCRVM | LIGKKNSPQE | EVELKKLKHL | EKSVEKIANQ | LEELNKELTG | 100 |
|  | IQQGFLPKDL | QAEALCKLDR | RVKATIEQFM | KILEEIHTLI | LPENFKDSRL | 150 |
|  | KRKGLVKKVQ | AFLAECDIVE | QNICQETERL | QSTNFALAE |  | 189 |

FIG. 4

```
                                                                 20
                                                                 50
hs33.pep  L--------- ---------- ---------- ---------- VTSQQGSS   EPVVQDLAQV
ms33.pep  MAKTEEMVQT EEMETPRLSV IVTHSNERYD LIVTPQGNS             EPVVQDLAQL 70
                                                                100
hs33.pep  VEEVIGVPQS FQKLIFKGKS LKEMETPLSA LGIQ GCRVM LIGKNSPQE
ms33.pep  VEEATGVPLP FQKLIFKGKS LKEMETPLSA LGVQ NGCRVM LIGKSNPFE 120
                                                                150
hs33.pep  EVELKKLKH  EKSMEKIANQ LELNKELIG  IQQGFLAKIL QAEALCKLDR
ms33.pep  EVELKKLKL  EVSPEKIANH LQELNKELSG IQQGFLAKSL QAEALCKLDR 170
                                                                200
hs33.pep  KVKATIEQFM KILEEIHLI  LPENFKDSRL KRKGLVKKVQ PFLAECDTVE
ms33.pep  KVKATIEQFM KILEEIHMV  LPEQFKDSRL KRKNLVKKVQ MFLAECDTVE 189
                                                                219
hs33.pep  QICQETERL  QSTNFALAE
ms33.pep  QICQETERL  QSTNIALAE
```

FIG. 5

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1054 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
CGCCTGCAAG   CCGCGGGTGA   AGAAGAAAGT   CCGGCCCCGC   TCTTCTCAGA   GCGAGAAGGT        60

AGGGAGCAGC   AGCAGGGAGT   TGACTAGAAG   TAAGAAAGTG   ACCCGTAGCA   AGAACGTGAC       120

CGGGACCCAG   GTAGAGGAGG   TGACCAAGAT   CGAGGAGGCG   ACCCAAACCG   AGGAAGTAAC       180
```

| | | | | | |
|---|---|---|---|---|---|
| TGTGGCAGAA | GAGGTGACCC | AGACCGACAA | CATGGCCAAG | ACCGAGGAGA | TGGTCCAGAC | 240 |
| GGAGGAAATG | GAAACACCCA | GACTCAGCGT | GATCGTCACC | CACAGCAATG | AGAGGTATGA | 300 |
| CCTTCTTGTT | ACCCCACAGC | AAGGTAACAG | TGAGCCAGTT | GTCCAAGACT | GGCTCAGCT | 360 |
| TGTTGAAGAG | GCCACAGGAG | TTCCACTACC | TTTTCAGAAG | CTCATATTTA | AGGGAAAATC | 420 |
| TCTGAAAGAA | ATGGAAACAC | CGTTGTCAGC | ACTTGGAATG | CAAAATGGTT | GCCGAGTCAT | 480 |
| GTTAATTGGT | GAAAAGAGCA | ATCCAGAAGA | AGAGGTTGAG | TTAAAGAAGC | TGAAAGATTT | 540 |
| GGAGGTATCT | GCAGAGAAGA | TAGCTAACCA | CCTGCAAGAA | TTGAATAAAG | AGCTTTCTGG | 600 |
| CATCCAGCAG | GGTTTTCTGG | CTAAGGAATT | GCAAGCGGAG | GCTCTCTGCA | AACTTGATAG | 660 |
| GAAAGTAAAA | GCAACAATTG | AGCAATTCAT | GAAGATCTTG | GAGGAGATTG | ACACAATGGT | 720 |
| CCTACCAGAA | CAATTTAAAG | ACAGCAGGCT | AAAAAGGAAG | AATTTGGTGA | AAAAGGTTCA | 780 |
| GGTGTTCTTA | GCAGAGTGTG | ACACAGTGGA | GCAATACATC | TGCCAAGAGA | CAGAGCGGCT | 840 |
| GCAGTCTACA | AACTTGGCCC | TGGCTGAATG | AAGTGCAGTG | GAGAGTGGCT | GTACTGGCCT | 900 |
| GAAGAGCAGC | TTTACAGCCC | TGCCCTCTCT | GGAACAGAAG | TCGCCTGTTT | CTCCATGGCT | 960 |
| GCCAGGGGCA | ACTAGCCAAA | TGTCAATTTC | CCTGCTCCTC | CGTCGGTTCT | CAATGAAAAA | 1020 |
| GTCCTGTCTT | TGCAACCTGA | AAAAAAAAAA | AAAA | | | 1054 |

( 2 ) INFORMATION FOR SEQ ID NO:2:

( i ) SEQUENCE CHARACTERISTICS:
( A ) LENGTH: 219 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

```
Met Ala Lys Thr Glu Glu Met Val Gln Thr Glu Glu Met Glu Thr Pro
1               5                  10                  15

Arg Leu Ser Val Ile Val Thr His Ser Asn Glu Arg Tyr Asp Leu Leu
            20                  25                  30

Val Thr Pro Gln Gln Gly Asn Ser Glu Pro Val Val Gln Asp Leu Ala
        35                  40                  45

Gln Leu Val Glu Glu Ala Thr Gly Val Pro Leu Pro Phe Gln Lys Leu
    50                  55                  60

Ile Phe Lys Gly Lys Ser Leu Lys Glu Met Glu Thr Pro Leu Ser Ala
65                  70                  75                  80

Leu Gly Met Gln Asn Gly Cys Arg Val Met Leu Ile Gly Glu Lys Ser
            85                  90                  95

Asn Pro Glu Glu Glu Val Glu Leu Lys Lys Leu Lys Asp Leu Glu Val
        100                 105                 110

Ser Ala Glu Lys Ile Ala Asn His Leu Gln Glu Leu Asn Lys Glu Leu
    115                 120                 125

Ser Gly Ile Gln Gln Gly Phe Leu Ala Lys Glu Leu Gln Ala Glu Ala
    130                 135                 140

Leu Cys Lys Leu Asp Arg Lys Val Lys Ala Thr Ile Glu Gln Phe Met
145                 150                 155                 160

Lys Ile Leu Glu Glu Ile Asp Thr Met Val Leu Pro Glu Gln Phe Lys
                    165                 170                 175

Asp Ser Arg Leu Lys Arg Lys Asn Leu Val Lys Lys Val Gln Val Phe
            180                 185                 190

Leu Ala Glu Cys Asp Thr Val Glu Gln Tyr Ile Cys Gln Glu Thr Glu
```

```
                    195                    200                      205
        Arg  Leu  Gln  Ser  Thr  Asn  Leu  Ala  Leu  Ala  Glu
                    210                    215
```

( 2 ) INFORMATION FOR SEQ ID NO:3:

( i ) SEQUENCE CHARACTERISTICS:
        ( A ) LENGTH: 733 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
CCTTCATGTT  ACCTCCCAGC  AGGGCAGCAG  TGAACCAGTT  GTCCAAGACC  TGGCCCAGGT     60
TGTTGAAGAG  GTCATAGGGG  TTCCACAGTC  TTTTCAGAAA  CTCATATTTA  AGGGAAAATC    120
TCTGAAGGAA  ATGGAAACAC  CGTTGTCAGC  ACTTGGAATA  CAAGATGGTT  GCCGGGTCAT    180
GTTAATTGGG  AAAAGAACA   GTCCACAGGA  AGAGGTTGAA  CTAAAGAAGT  TGAAACATTT    240
GGAGAAGTCT  GTGGAGAAGA  TAGCTAACCA  GCTGGAAGAG  TTGAATAAAG  AGCTTACTGG    300
AATCCAGCAG  GGTTTTCTGC  CCAAGGATTT  GCAAGCTGAA  GCTCTCTGCA  AACTTGATAG    360
GAGAGTAAAA  GCCACAATAG  AGCAGTTTAT  GAAGATCTTG  GAGGAGATTC  ACACACTGAT    420
CCTGCCAGAA  AATTTCAAAG  ACAGTAGATT  GAAAAGGAAA  GGCTTGGTAA  AAAAGGTTCA    480
GGCATTCCTA  GCCGAGTGTG  ACACAGTGGA  GCAGAACATC  TGCCAGGAGA  CTGAGCGGCT    540
GCAGTCTACA  AACTTTGCCC  TGGCCGAGTG  AGGTGTAGCA  GAAAAGGCT   GTGCTGCCCT    600
GAAGAATGGC  GCCACCAGCT  CTGCCGTCTC  TGGATCGGAA  TTTACCTGAT  TTCTTCAGGG    660
CTGCTGGGGG  CAACTGGCCA  TTTGCCAATT  TTCCTACTCT  CACACTGGTT  CTCAATGAAA    720
AATAGTGTCT  TTG                                                           733
```

( 2 ) INFORMATION FOR SEQ ID NO:4:

( i ) SEQUENCE CHARACTERISTICS:
        ( A ) LENGTH: 189 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Leu  His  Val  Thr  Ser  Gln  Gln  Gly  Ser  Ser  Glu  Pro  Val  Val  Gln  Asp
 1                  5                           10                          15

Leu  Ala  Gln  Val  Val  Glu  Glu  Val  Ile  Gly  Val  Pro  Gln  Ser  Phe  Gln
                    20                          25                      30

Lys  Leu  Ile  Phe  Lys  Gly  Lys  Ser  Leu  Lys  Glu  Met  Glu  Thr  Pro  Leu
                35                      40                      45

Ser  Ala  Leu  Gly  Ile  Gln  Asp  Gly  Cys  Arg  Val  Met  Leu  Ile  Gly  Lys
         50                      55                      60

Lys  Asn  Ser  Pro  Gln  Glu  Glu  Val  Glu  Leu  Lys  Lys  Leu  Lys  His  Leu
 65                          70                      75                      80

Glu  Lys  Ser  Val  Glu  Lys  Ile  Ala  Asn  Gln  Leu  Glu  Glu  Leu  Asn  Lys
                        85                      90                          95

Glu  Leu  Thr  Gly  Ile  Gln  Gln  Gly  Phe  Leu  Pro  Lys  Asp  Leu  Gln  Ala
                    100                     105                     110

Glu  Ala  Leu  Cys  Lys  Leu  Asp  Arg  Arg  Val  Lys  Ala  Thr  Ile  Glu  Gln
                115                     120                     125
```

```
Phe Met Lys Ile Leu Glu Glu Ile His Thr Leu Ile Leu Pro Glu Asn
    130             135             140

Phe Lys Asp Ser Arg Leu Lys Arg Lys Gly Leu Val Lys Lys Val Gln
145             150             155             160

Ala Phe Leu Ala Glu Cys Asp Thr Val Glu Gln Asn Ile Cys Gln Glu
            165             170             175

Thr Glu Arg Leu Gln Ser Thr Asn Phe Ala Leu Ala Glu
        180             185
```

BCL-2-ASSOCIATED PROTEINS

This application is a divisional of application Ser. No. 08/152,485, filed Nov. 11, 1993 now U.S. Pat. No. 5,539,094.

This work was supported by grant CA47956 awarded by the National Cancer Institute of the National Institutes of Health. The United States Government has certain rights in this invention.

BACKGROUND OF THE INVENTION

FIELD OF THE INVENTION

This invention relates generally to the fields of molecular biology and molecular medicine and more specifically to a novel protein that can regulate apoptosis.

BACKGROUND INFORMATION

The human body contains various tissues that continually undergo a process of self-renewal, whereby older cells in the tissue die and are replaced by new cells. In order to maintain a relatively constant number of cells in a particular tissue, it is important that the number of dying cells in a tissue is equivalent to the number of newly produced cells. This homeostasis is maintained by committing the cells in self-renewing tissues to a process of programmed cell death. The morphological features of cells undergoing this form of cell death has been termed "apoptosis." Though not all programmed cell deaths occur through apoptosis, as used herein, the terms "programmed cell death" and "apoptosis" are used interchangeably.

Defects in the process of apoptosis occur in various pathological conditions. For example, in cancer, a defect in apoptosis results in cancer cells surviving longer than their normal cell counterparts. As a result, the increased number of surviving cancer cells can cause an increase in the mass of a tumor, even if the doubling time of the cancer cells is not increased above normal. In viral infections, induction of apoptosis can figure prominently in the pathophysiology of the disease process.

A protein, termed Bcl-2, plays a central role in the process of programmed cell death by blocking apoptosis. For example, when Bcl-2 levels in a cell are elevated, apoptosis is blocked. Conversely, when Bcl-2 levels in a cell are lowered, the rate of cell death is accelerated. Bcl-2 likely exerts its apoptosis-blocking effect at a final common pathway leading to apoptotic cell death. However, the molecular mechanism by which Bcl-2 blocks apoptosis remains enigmatic. An understanding of the role of Bcl-2 in the process of apoptosis is complicated by the observation that Bcl-2 is undetectable in some cell types that undergo apoptosis.

The presence of Bcl-2 in a cell also renders the cell highly resistant to various chemical and physical agents. In particular, Bcl-2 renders cancer cells more resistant to chemotherapeutic agents. Recently, various cellular and viral gene products have been identified that share a similar structure or activity with Bcl-2. Despite the similarity of Bcl-2 to these Bcl-2-related proteins, however, no structural feature of the Bcl-2 protein has been identified that lends a clue to its mechanism of regulating apoptosis.

One possible way Bcl-2 may act in the process of apoptosis is by regulating the activity of another protein involved in apoptosis. If so, the identification of an interaction between such a protein and Bcl-2 would allow the exploitation of this interaction in an assay to screen for agents such as drugs that alter the interaction. Such an assay would allow the identification of drugs that can regulate apoptosis and are useful for treating diseases such as neurodegenerative diseases or cancer or for modifying the effectiveness of currently available cancer chemotherapeutic agents.

There thus exists need to identify and produce proteins that associate with Bcl-2 or Bcl-2-related proteins in order to modulate the regulation of apoptosis. The present invention satisfies this need and provides related advantages as well.

SUMMARY OF THE INVENTION

The present invention relates to a nucleic acid molecule encoding a protein or a fragment thereof that associates with Bcl-2 or a Bcl-2-related protein. The invention also relates to Bcl-2-associated proteins (BAP) such as Bcl-2-associated protein-1 (BAP-1), which binds to Bcl-2, and to antibodies specific for a BAP.

The invention also relates to methods for detecting agents such as drugs that decrease or inhibit the binding of a BAP with Bcl-2 or a Bcl-2-related protein and to methods for detecting agents that induce the dissociation of a bound complex formed by the association of a BAP and a Bcl-2-related protein.

The invention further relates to methods for modulating the activity of Bcl-2 or a Bcl-2-related protein in a cell by introducing into the cell a nucleic acid encoding a BAP or by introducing into a cell an antisense nucleotide sequence, which is complementary to a region of a gene encoding a BAP and can hybridize to a BAP gene in a cell or to an mRNA transcribed from the gene.

BRIEF DESCRIPTION OF THE DRAWINGS

FIG. 1 (SEQ. ID. NO. 1) shows the mouse Bcl-2-associated protein cDNA sequence.

FIG. 2 (SEQ. ID. NO. 2) shows the 219 amino acid sequence for the mouse Bcl-2-associated protein, as deduced from the open reading frame present in the nucleic acid sequence shown in FIG. 1.

FIG. 3 (SEQ. ID. NO. 3) shows a cDNA sequence encoding a portion of the human Bcl-2-associated protein.

FIG. 4 (SEQ. ID. NO. 4) shows a 189 amino acid portion of the human Bcl-2-associated protein, as deduced from the open reading frame present in the nucleic acid sequence shown in FIG. 3.

FIG. 5 illustrates the amino acid sequence identity shared among mouse BAP-1 (mS33ORF.pep) and human (hs33.pep) BAP-1.

DETAILED DESCRIPTION OF THE INVENTION

Figure 6:
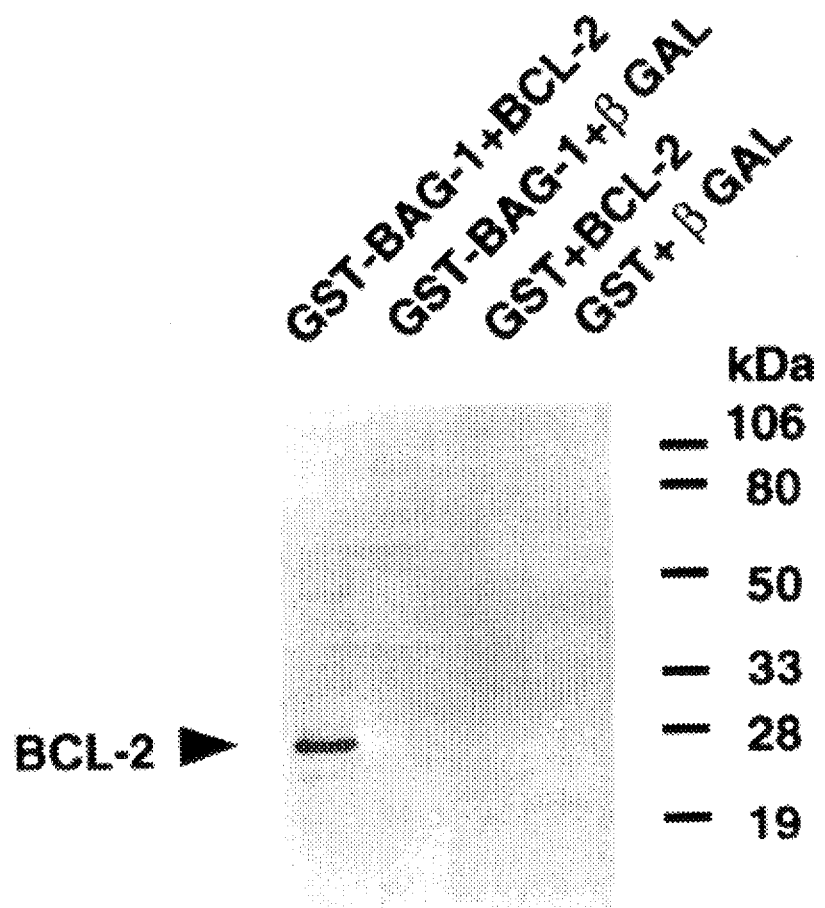
FIG. 6 shows the migration of Bcl-2, which was isolated by virtue of its association with BAP-1.

The present invention provides nucleic acid molecules encoding proteins or fragments thereof that bind to Bcl-2 or to Bcl-2-related proteins. The invention also provides Bcl-2-associated proteins (BAP) such as Bcl-2-associated protein-1 (BAP-1), which binds to Bcl-2.

Bcl-2 prolongs cell survival by blocking apoptosis. In addition to maintaining homeostasis in self-renewing tissues, Bcl-2 likely is involved in immune cell "education" and the elimination of redundant neurons and other cell types during development. Bcl-2, which is an acronym for the protein encoded by the B cell lymphoma/leukemia-2 gene, was identified by virtue of its involvement in the t(14:18) translocation, which is characteristic of a form of B cell lymphoma, and gene transfer experiments have demonstrated that Bcl-2 has oncogenic potential in a cell. As used herein, the term "Bcl-2" refers to the protein and the term "bcl-2" refers to the gene encoding Bcl-2. In cancer cells, Bcl-2 expression can result in increased cell survival, which contributes to the tumor mass.

Bcl-2 action occurs even in the complete absence of cell proliferation. Overexpression of Bcl-2 in a cell reduces the requirement of "competence" factors such as platelet derived growth factor and epidermal growth factor for growth of the cell in culture. Overexpression of Bcl-2 does not, however, affect the dependence of cells in culture on "progression" factors such as insulin-like growth factor-1. The role of Bcl-2 in apoptosis has been confirmed by showing that cells in which Bcl-2 levels are decreased due to expression of an antisense bcl-2 nucleic acid sequence have an accelerated rate of cell death. However, decreased Bcl-2 levels, alone, are not sufficient to cause cell death in many types of cells.

The present invention provides a nucleic acid molecule that encodes a BAP, which can associate with Bcl-2 or a Bcl-2-related protein and, thus, can be involved in the regulation of apoptosis. The invention provides, for example, a cDNA encoding mouse BAP-1 (FIG. 1; SEQ. ID. NO. 1). The mouse BAP-1 cDNA was cloned from a bacteriophage lambda EXLox expression vector library, which was screened using a recombinant Bcl-2 protein and an antibody to Bcl-2. Essentially, mouse cDNA was cloned into the lambda EXLox bacteriophage and the cDNA was expressed in *E. coli*. The resultant plaques were screened using a recombinant Bcl-2 protein and binding of Bcl-2 was identified using an anti-Bcl-2 antibody, which was prepared as described by Reed et al., *Anal. Biochem.* 205:70–76 (1992)), which is incorporated herein by reference. Positive phage were isolated and the cDNA inserts were sequenced. An 833 base pair cDNA was obtained and used to screen two other mouse cDNA libraries. The mouse BAP-1 cDNA sequence shown in FIG. 1 as obtained using this cloning strategy.

Although the lambda EXLox expression system was used to obtain the described mouse BAP-1 cDNA, other expression vector systems such as lambda gt11 can be used to clone and express a cDNA such as the mouse BAP-1 cDNA (see, for example, Sambrook et al., *Molecular Cloning: A laboratory manual* (Cold Spring Harbor Laboratory Press (1989), which is incorporated herein by reference). In addition, various other cloning and expression vectors are well known in the art and can be purchased from commercial sources.

Nucleic acid probes based on the mouse BAP-1 cDNA sequence of FIG. 1 can be used to screen a cDNA or genomic DNA library to obtain a nucleic acid encoding mouse BAP-1 or a BAP-1 cDNA from another species such as human. For example, oligonucleotides corresponding to a nucleotide sequence present, for example, in FIG. 1 can be synthesized using routine methods and used as hybridization probes to screen a library for a nucleic acid molecule having homology with the cDNA sequence encoding mouse BAP-1 (see Sambrook et al., Chap. 11 (1989)). Oligonucleotides having a specific nucleotide sequence, including degenerate nucleotide sequences as desired, also can be purchased from commercial sources. One skilled in the art would know that a screening method utilizing, for example, such oligonucleotides requires that hybridization be performed under relatively stringent conditions such that hybridization is relatively specific.

Oligonucleotide probes also can be used to identify genetic defects due a mutation of a BAP-1 gene in a cell. Such a genetic defect can lead to aberrant expression of BAP-1 in a cell or to expression of an aberrant BAP-1, which does not properly associate with a Bcl-2-related protein in the cell. As a result, a genetic defect in a BAP-1 gene can result in a pathology characterized by increased or decreased apoptosis. Oligonucleotide probes consisting of a nucleotide sequence of the nucleic acid molecules disclosed herein can be used to identify cells having a mutation in a BAP-1 gene using well known hybridization methods. In order to provide the specificity necessary to identify, for example, a point mutation in a BAP-1 gene, one skilled in the art would know that an oligonucleotide probe should be at least about fourteen to sixteen nucleotides in length (Sambrook et al. 1989)). In addition, the probe should incorporate a detectable moiety such as a radiolabel, a fluorochrome or a detectable binding agent such as biotin. Various detectable moieties and methods of incorporating the moiety into an oligonucleotide probe are well known in the art and are commercially available.

The invention also provides a cDNA encoding a portion of human BAP-1 (FIG. 3; SEQ. ID. NO. 3). The human BAP-1 cDNA was obtained using the mouse BAP-1 cDNA as a hybridization probe to screen a human cDNA library. Positive clones were sequenced and the cDNA sequence shown in FIG. 3 was obtained. The human cDNA sequence was used, in turn, as a hybridization probe to screen a human cosmid library using methods as described below or otherwise known in the art (see, for example, in Sambrook et al. (1989)). Two positive cosmid clones were isolated and the DNA inserts from the cosmids were used as probes for in situ hybridization to determine the chromosomal location of the human BAP-1 gene. Using this method, the human BAP-1 gene was localized to chromosome 9 at approximately band p13.

Since the amino acid sequences of the mouse and human BAP-1 proteins can be determined from the cloned nucleotide sequences shown in FIGS. 1 and 3, one skilled in the art can readily determine equivalent nucleotide sequences that also encode mouse and human BAP-1. As used herein, an "equivalent" nucleotide sequence means a sequence that is different from that shown in FIG. 1 or 3, but which encodes a protein having the identical amino acid sequence as shown in FIG. 2 or 4, respectively. An equivalent nucleotide sequence is readily constructed by incorporating silent nucleotide changes into a nucleotide sequence of FIG. 1 or 3. Silent nucleotide changes are well known in the art and result from the degeneracy of the genetic code. One skilled in the art would readily recognize that a nucleotide sequence that is equivalent to a sequence as shown in FIG. 1 or 3 would encode a polypeptide as shown in FIG. 2 or 4, respectively.

The invention also provides mouse Bcl-2-associated protein-1 (BAP-1) and human BAP-1. The amino acid sequences of these polypeptides were deduced from the nucleic acid sequences shown in FIGS. 1 and 3, respectively. The 219 amino acid mouse BAP-1 sequence is shown in FIG. 2 (SEQ. ID. NO. 2) and a 189 amino acid portion of the human BAP-1 protein is shown in FIG. 4 (SEQ. ID. NO. 4). A comparison of the amino acid sequences for mouse and human BAP-1 reveals that the two polypeptides share extensive sequence identity (FIG. 5).

As used herein, the term "polypeptide" is used in its broadest sense to include proteins, polypeptides and peptides, which are related in that each consists of a sequence of amino acids joined by peptide bonds. While no specific attempt is made to distinguish the size limitations, for example, of proteins and peptides, one skilled in the art would understand that proteins generally consist of at least about 50 to 100 amino acids and that peptides generally consist of at least two amino acids up to a few dozen amino acids. The term polypeptide as used herein includes any such amino acid sequence.

The invention also provides active fragments of BAP-1. As used herein, an "active fragment" of BAP-1 is a polypeptide that consists of an amino acid sequence derived from a BAP protein as shown, for example, in FIGS. 2 and 4 and that has the ability to associate with a Bcl-2-related protein. Active fragments of a BAP are readily identified using the methods described in detail below. A particularly useful method for obtaining active fragments of BAP-1 is to create peptide libraries as described, for example, in U.S. Pat. No. 5,223,409, which is incorporated herein by reference, and screening such libraries with a Bcl-2-related protein as described in Example I.

A BAP is defined primarily by its ability to associate in vitro and in vivo with Bcl-2-related proteins. As used herein, the term "associate" means that a BAP and a Bcl-2-related protein have a binding affinity for each other such that the BAP and the Bcl-2-related protein form a bound complex. The affinity of binding of a BAP and a Bcl-2-related protein is sufficiently specific such that the bound complex can form in vivo in a cell and, can form in vitro under appropriate conditions, as described herein. The formation or dissociation of a bound complex can be identified as described in Example VII or using other well known methods such as equilibrium dialysis.

As described herein, mouse BAP-1 and human BAP-1 are examples of a Bcl-2-associated protein. Other examples of a BAP include the Raf-related proteins such as A-Raf, B-Raf or the Raf-1 kinase, which is a serine/threonine-specific kinase having a molecular mass of about 72 to 74 kDa. The Raf-1 kinase, for example, has an amino-terminal regulatory domain and a carboxyl-terminal catalytic domain. Removal of the regulatory domain by deletional mutagenesis releases the catalytic domain from suppression and produces a kinase having a constitutively high level of enzymatic activity (Heidecker et al., Mol. Cell. Biol. 10:2503–2512 (1990), which is incorporated herein by reference). In some cell types and under some conditions, the presence of Bcl-2 alone is not sufficient to block apoptosis. However, whereas neither Bcl-2 nor Raf-1 alone can suppress apoptosis, the combination of Bcl-2 and the Raf-1 kinase suppresses apoptosis. As described in Example VI, below, Raf-1 associates with Bcl-2 in vivo and, therefore, has the characteristics of a Bcl-2-associated protein.

As used herein, the term "Bcl-2-related" proteins refers to proteins that are structurally or functionally related to Bcl-2. Bcl-2-related proteins can be identified by their ability to associate with a BAP such as BAP-1 under appropriate conditions (Example III). Several genes encoding Bcl-2-related proteins are known. For example, the bcl-2 gene is highly homologous to bcl-X, which encodes two proteins, Bcl-X-L and Bcl-X-S, formed via alternative splicing. Bcl-2 also has a weak homology with an open reading frame, BHRF-1, in Epstein Barr Virus (Cleary et al., Cell 47:19–28 (1986), which is incorporated herein by reference) and with the C. elegans ced-9 gene, which, when overexpressed, prevents programmed cell deaths during worm development (Hengartner et al., Nature 356:494–499 (1992); Vaux et al., Science 258:1955–1957 (1992), each of which is incorporated herein by reference). In addition, the mcl-1 gene and the A1 gene, which have moderate homology with bcl-2 and BHRF-1, are Bcl-2-related proteins that have been identified in leukemic and normal myeloid cells, respectively, that were induced to differentiate using phorbol ester or colony stimulating factors (see, for example, Lin et al., J. Immunol. 151:1979–1988 (1993), which is incorporated herein by reference). Although the function of these Bcl-2-related genes has not been described, the mcl-1 and A1 gene products may have roles in apoptosis in cells. Bcl-2β, which is an alternatively spliced form of Bcl-2, is another example of a Bcl-2-related protein.

In view of the nucleic acid sequences encoding BAP-1 and the BAP-1 amino acid sequences that are provided herein, one skilled in the art would know how to synthesize specific BAP-1 peptides or an entire BAP-1 protein, if desired, using routine methods of solid phase peptide synthesis (see Example IV). In addition, analogs of BAP-1 or BAP-1 peptides can be designed to have increased stability in vivo or in vitro or higher or lower affinity of binding to a Bcl-2-related protein by incorporating, for example, (D)-amino acids into a BAP-1 peptide or by chemically modifying reactive amino acid side chains or the amino or carboxy terminus of a peptide. For example, a reactive amino group in a peptide can be rendered less reactive by acetylation. Furthermore, a modification such as acetylation changes a hydrophilic group to a hydrophobic group, which can be advantageous, for example, when it is desirable to prepare a BAP-1 peptide that can readily traverse a cell membrane.

The invention further provides antibodies specific for BAP-1. As used herein, the term "antibody" is used in its broadest sense to include polyclonal and monoclonal antibodies, as well as polypeptide fragments of antibodies that retain a specific binding activity for a BAP of at least about $1 \times 10^5 M^{-1}$. One skilled in the art would know that anti-HAP-1 antibody fragments such as Fab, F(ab')$_2$ and Fv fragments can retain specific binding activity for HAP-1 and, thus, are included within the definition of an antibody. In addition, the term "antibody" as used herein includes naturally occurring antibodies as well as non-naturally occurring antibodies and fragments that retain binding activity. Such nonnaturally occurring antibodies can be constructed using solid phase peptide synthesis, can be produced recombinantly or can be obtained, for example, by screening combinatorial libraries consisting of variable heavy chains and variable light chains as described by Huse et al., Science 246:1275–1281 (1989), which is incorporated herein by reference.

As described in Example IV, below, anti-BAP-1 antibodies were prepared using a BAP-1 fusion protein as immunogen. However, one skilled in the art would know that purified BAP-1, which can be prepared from natural sources or produced recombinantly, or fragments of BAP-1 including synthetic peptides as described above can be used as an immunogen. Non-immunogenic fragments or synthetic peptides of BAP-1 can be made immunogenic by coupling the hapten to a carrier molecule such bovine serum albumin (BSA) or keyhole limpet hemocyanin (KLH), as described in Example IV, below. In addition, various other carrier molecules and methods for coupling a hapten to a carrier molecule are well known in the art and described, for example, by Harlow and Lane, Antibodies: A laboratory manual (Cold Spring Harbor Laboratory Press, 1988), which is incorporated herein by reference.

Since BAP-1 and Bcl-2, for example, associate in a cell in vivo (see Example V), a pathology that is characterized by an increased or decreased level of apoptosis, as compared to the level of apoptosis known to occur in a healthy tissue, may be due to an increased or decreased level of BAP-1 in a cell. Thus, it can be desirable to determine whether BAP-1 levels in a cell are within the normal range expected for a particular cell type in a tissue or organ. Anti-BAP-1 antibodies are useful for determining the level of BAP-1 in a tissue sample, which can be diagnostic of a pathology. Such a determination can be made using immunoassay and immunohistochemical methods as described in Example V or otherwise known in the art (see, for example, Reed et al. (1992); see, also, Harlow and Lane (1988)).

A diagnostic kit incorporating an anti-BAP-1 antibody as an assay for detecting a pathology due to altered BAP-1 expression in a cell is particularly useful. Such a kit can contain, in addition to an anti-BAP-1 antibody, a reaction cocktail that provides the proper conditions for performing the assay, control samples that contain known amounts of BAP-1 and, if desired, a second antibody specific for the anti-BAP-1 antibody. A diagnostic assay should include a simple method for detecting the amount of BAP-1 in a sample that is bound to the antibody. Detection can be performed by labelling an anti-BAP-1 antibody using methods well known in the art (see, for example, Harlow and Lane, 1988; chap. 9). For example, an antibody can be labelled with various detectable moieties including a radiolabel, an enzyme, biotin or a fluorochrome. Reagents for labelling an anti-BAP-1 antibody can be included in the diagnostic kit or can be purchased separately from a commercial source. Following contact of a labelled antibody with a sample such as a tissue homogenate or a histological section of a tissue, specifically bound labelled antibody can be identified by detecting the particular moiety.

Alternatively, a labelled second antibody can be used to identify specific binding of an unlabelled anti-BAP-1 antibody. A second antibody generally will be specific for the particular class of the first antibody. For example, if an anti-BAP-1 antibody is of the IgG class, a second antibody will be an anti-IgG antibody. Such second antibodies are readily available from commercial sources. The second antibody can be labelled using a detectable moiety as described above. When a sample is labelled using a second antibody, the sample is first contacted with a first antibody, then the sample is contacted with the labelled second antibody, which specifically binds to the first antibody and results in a labelled sample.

Example IV provides a detailed method for raising polyclonal anti-BAP-1 antibodies in rabbits. In addition, monoclonal antibodies can be obtained using methods that are well known and routine in the art (Reed et al. (1992); Harlow and Lane (1988)). Essentially, spleen cells from a BAP-1-immunized mouse can be fused to an appropriate myeloma cell line such as SP/02 myeloma cells to produce hybridoma cells. Cloned hybridoma cell lines can be screened using labelled BAP-1 protein to identify clones that secrete anti-BAP-1 monoclonal antibodies and hybridomas that express antibodies having a desirable specificity and affinity can be isolated and utilized as a continuous source of anti-BAP-1 antibodies. One skilled in the art would know that a dependable source of monoclonal anti-BAP-1 antibodies is desirable, for example, for preparing diagnostic kits as described above.

The invention further provides methods for detecting agents such as drugs that can alter the ability of a BAP to associate with a Bcl-2-related protein and methods for detecting agents that induce dissociation of a bound complex formed by the association of a BAP and a Bcl-2-related protein. An example of a screening assay for detecting such agents is provided in FIG. 7 and is described in Example VII.

As used herein, the term "agent" means a chemical compound that can be useful as a drug. The screening assay described herein is particularly useful in that it can be automated, which allows for high through-put screening of randomly designed agents to identify useful drugs, which can alter the ability of a BAP and a Bcl-2-related protein to associate. For example, a drug can alter the ability of a BAP and a Bcl-2-related protein to associate by decreasing or inhibiting the binding affinity of a BAP and a Bcl-2-related protein. Such a drug can be useful where it is desirable to increase the concentration of unbound Bcl-2 in a cell, for example, so that free Bcl-2 is available to block apoptosis. Alternatively, a drug can be useful for increasing the affinity of binding of a BAP and a Bcl-2-related protein.

Figure 7:
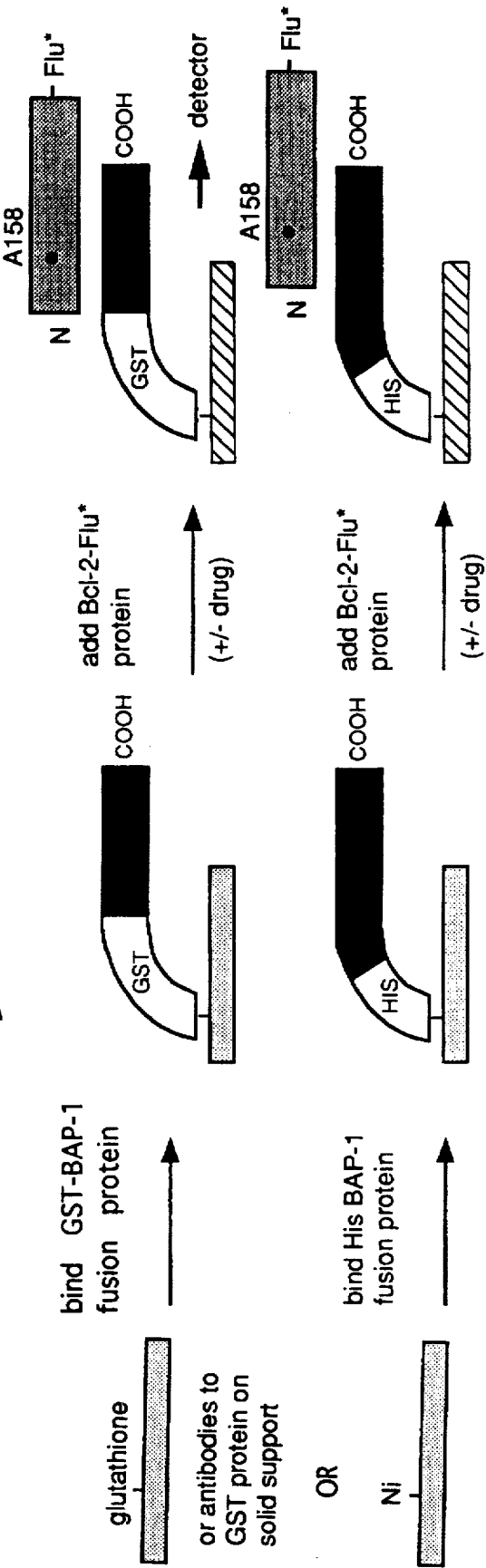
FIG. 7 presents a schematic diagram of a method for screening drugs that can alter the association of a BAP and a Bcl-2-related protein.

The drug screening assay can utilize BAP-1 or, as exemplified in FIG. 7, a BAP-1 fusion protein such as a BAP-1-glutathione-S-transferase (GST) or BAP-1-histidine-6 fusion protein (see Example II). The BAP-1 or BAP-1 fusion protein is characterized, in part, by having an affinity for a solid substrate as well as having an affinity for a Bcl-2-related protein. For example, when BAP-1 is used in the assay, the solid substrate can contain a covalently attached anti-BAP-1 antibody. Alternatively, a BAP-1-GST fusion protein can be used in the assay. Where such a fusion protein is used in the assay, the solid substrate can contain covalently attached glutathione, which is bound by the GST component of the BAP-1-GST fusion protein.

The drug screening assay can be performed by allowing the BAP or BAP-fusion protein to bind to the solid support, then adding a Bcl-2-related protein and a drug to be tested (see Example VII). Control reactions will not contain the drug (see Examples II and III). Following incubation of the reaction mixture under conditions known to be favorable for the association, for example, of BAP-1 and Bcl-2 in the absence of a drug, the amount of Bcl-2 specifically bound to BAP-1 in the presence of a drug can be determined. For ease of detecting binding, the Bcl-2 protein can be labelled with a detectable moiety, such as a radionuclide or a fluorescent label, as described above and in Example VII, below. By comparing the amount of specific binding of BAP-1 and Bcl-2 in the presence of a drug as compared to the control level of binding, a drug that increases or decreases the binding of a BAP and a Bcl-2-related protein can be identified. Thus, the drug screening assay provides a rapid and simple method for selecting drugs having a desirable effect on the association of a BAP and a Bcl-2-related protein.

The invention further provides methods for modulating the activity of Bcl-2 or a Bcl-2-related protein in a cell by introducing into the cell a nucleotide sequence encoding BAP-1 or an antisense nucleotide sequence, which is complementary to a region of a gene encoding BAP-1 and can hybridize to the gene or to an mRNA transcribed from the gene. As used herein, the term "modulate" means the level of a BAP expressed in a cell can be increased or decreased. Thus, the compounds described herein can be used as medicaments for the treatment of a pathology caused by an altered level of apoptosis.

The level of a gene product such as BAP-1 can be increased in a cell using recombinant expression vectors and gene transfer technology to express a nucleic acid encoding BAP-1 or an active fragment of BAP-1. Various expression vectors and methods for introducing such vectors into a cell are well known in the art and are described, for example, in Sambrook et al. (1989). Viral vectors that are compatible with a targeted cell are particularly useful for introducing a nucleic acid encoding BAP-1 into a cell. For example, recombinant adenoviruses having general or tissue-specific promoters can be used to deliver BAP-1 expression constructs into a variety of types of tissues and cells, including non-mitotic cells, and to drive BAP-1 cDNA expression in the target cells. Recombinant adeno-associated viruses also are useful and have the added advantage that the recombinant virus can stably integrate into the chromatin of even quiescent non-proliferating cells such as neurons of the central and peripheral nervous systems (Lebkowski et al., *Mol. Cell. Biol.* 8:3988–3996 (1988), which is incorporated herein by reference).

Such viral vectors are particularly useful where one skilled in the art desires to provide a nucleic acid encoding BAP-1 to a subject, for example, for gene therapy. Viruses are specialized infectious agents that have evolved in many cases to elude host defense mechanisms and to infect and propagate in specific cell types. The targeting specificity of viral vectors can be utilized to target predetermined cell types and introduce a recombinant gene into the infected cell. Thus, the viral vector selected will depend, in part, on the cell type to be targeted. For example, if neurodegenerative diseases are to be treated by increasing the BAP-1 levels in neuronal cells affected by a disease, then a vector specific for cells of the neuronal cell lineage can be used. Such viral vectors include, for example, Herpes simplex virus-based vectors (Battleman et al., *J. Neurosci.* 13:941–951 (1993), which is incorporated herein by reference). Similarly, if a disease or pathological condition of the hematopoietic system is to be treated, then a viral vector that is specific for blood cells and their precursors, preferably for the specific type of hematopoietic cell, can be used. Such viral vectors include, for example, HIV-based vectors (Carroll et al., *J. Cell. Biochem.* 17E:241 (1993), which is incorporated herein by reference).

Vectors such as those described herein also can express specific receptors or ligands, which can modify or alter target specificity through receptor mediated events. Such vectors can be constructed using recombinant DNA techniques or synthetic chemistry procedures. In addition, a viral vector can be made tissue-specific by incorporating a tissue-specific promoter or enhancer into the vector (Dai et al., *Proc. Natl. Acad. Sci. USA* 89:10892–10895 (1992), which is incorporated herein by reference).

Retroviral vectors are often preferred for in vivo targeting and therapy procedures. Retroviral vectors can be constructed either to function as infectious particles or to undergo only a single initial round of infection. In the former case, the genome of the virus is modified so that it maintains the necessary genes, regulatory sequences and packaging signals to synthesize new viral proteins and RNA. However, genes conferring oncogenic potential of these viruses is destroyed. After the viral proteins are synthesized, the host cell packages the RNA into new viral particles, which can undergo further rounds of infection. The viral genome also is engineered to encode and express the desired recombinant gene.

In the case of non-infectious viral vectors, the helper virus genome is usually mutated to destroy the viral packaging signal required to encapsulate the RNA into viral particles. However, the helper virus retains structural genes required to package a co-introduced recombinant virus containing a gene of interest. Without a packaging signal, viral particles will not contain a genome and, thus, cannot proceed through subsequent rounds of infection.

Methods for constructing and using viral vectors are known in the art and are reviewed, for example, in Miller and Rosman, *Biotechniques* 7:980–990 (1992), which is incorporated herein by reference. The specific type of vector will depend upon the intended application. These vectors are well known and readily available within the art or can be constructed by one skilled in the art.

For gene therapy, BAP-1-encoding expression vectors can be administered to a subject in several ways to obtain increased levels of BAP-1 in the cells affected by a disease or pathological condition. For example, if viral vectors are used, the procedure can take advantage of their target specificity and the vectors need not be administered locally at the diseased site. However, local administration can provide a quicker, more effective treatment. Administration also can be by intravenous or subcutaneous injection into the subject. Injection of viral vectors into the spinal fluid can be used as a mode of administration, especially in the case of neurodegenerative diseases. Following injection, the viral vectors will circulate until they recognize host cells with the appropriate target specificity for infection.

Receptor-mediated DNA delivery approaches also can be used to deliver BAP-1 expression plasmids into cells in a tissue-specific fashion using a tissue-specific ligand or antibody non-covalently complexed with DNA via bridging molecules (Curiel et al., *Hum. Gene Ther.* 3:147–154 (1992); Wu and Wu, *J. Biol. Chem.* 262:4429–4432 (1987), each of which is incorporated herein by reference). Direct injection of DNA or DNA encapsulated in cationic liposomes also can be used for stable gene transfer to non-dividing and dividing cells in vivo (Ulmer et al., *Science* 259:1745–1748 (1993), which is incorporated herein by reference). In addition, DNA can be transferred into a variety of tissues using the particle bombardment method (Williams et al., *Proc. Natl. Acad. Sci. USA* 88:2726–2730 (1991), which is incorporated herein by reference).

A particularly useful mode of administration of BAP-1 encoding vectors is by direct inoculation locally at the site of the disease or pathological condition. Local administration is advantageous because there is no dilution effect and, therefore, a smaller dose is required to achieve BAP-1 expression in a majority of the targeted cells. Additionally, local inoculation can alleviate the targeting requirement necessary with other forms of administration. Thus, a vector that infects all cells in the inoculated area can be used. If expression is desired in only a specific subset of cells within the inoculated area, then promoter and expression elements that are specific for the desired subset can be used to accomplish this goal. Such non-targeting vectors can be viral vectors, viral genomes, plasmids, phagemids and the like. Transfection vehicles such as liposomes also can be used to introduce the non-viral vectors described above into recipient cells within the inoculated area. Such transfection vehicles are well known in the art. Transfection methods also are useful for introducing a BAP-1-containing vector into a cell in culture. Such methods, including calcium phosphate precipitation, DEAE-dextran facilitated transfection and lipofection methods are well known in the art and reagents for performing these methods are commercially available (Sambrook et al. (1989)).

The level of BAP-1 in a cell also can be modulated such that BAP-1 levels in the cell are decreased. As a consequence of decreased BAP-1 levels, free Bcl-2 levels in a cell are increased. Various methods using, for example, ribozymes or homologous recombinant gene knock-out can be used to decrease the level of BAP-1 in a cell (see, for example, Capecchi, *Nature* 344:105 (1990) and references cited therein; McCall et al., *Proc. Natl. Acad. Sci., USA* 89:5710–5714 (1992), each of which is incorporated herein by reference). One method for decreasing the expression of a protein such as BAP-1 in a cell is to introduce into the cell an antisense RNA-producing expression vector or synthetic antisense oligonucleotides, which are complementary to a nucleotide sequence of a BAP-1 gene (see, for example, Godson et al., *J. Biol. Chem.* 268:11946–11950 (1993); Reed et al., *Canc. Res.* 50:6565–6570 (1990a); Reed et al., *Proc. Natl. Acad. Sci., USA* 87:3660–3664 (1990b), each of which is incorporated herein by reference). Antisense oligonucleotides can be purchased or can be synthesized as described above.

Antisense RNA can be produced in a cell using expression vectors as described above. In this case, expression from the vector can result, for example, in the production of antisense RNA in a cell (see Reed et al. (1990b)). Alternatively, synthetic antisense oligonucleotides can be introduced directly into cells or can be encapsulated, for example, in liposomes, which facilitate transfer of oligonucleotides into a cell. Where antisense oligonucleotides are directly administered, it can be desirable to construct the oligonucleotides using nucleotide analogs, which can confer increased stability on the oligonucleotide in vivo, as described, for example, by Reed et al. (1990a)).

Expression of a BAP in a cell also can provide a therapeutic advantage in treating a subject such as a cancer patient with a chemotherapeutic agent. Bcl-2 expression in a cell has been found to prevent or markedly reduce cell killing induced by a wide variety of physical and chemical agents including, for example, 1) calcium ionophores, phorbol esters, cAMP derivatives, anti-T cell receptor complex antibodies and glucocorticoids in primary thymocytes and leukemic T cell lines; 2) gamma-irradiation in immature hematolymphoid cells; 3) heat shock; 4) glucose deprivation, free radicals, lipid peroxidation and glutamate in PC12 rat pheochromocytoma and other neuronal cell lines; 5) some type of viruses including baculovirus in insect cells and Sindbis virus in mammalian cells; and 6) various chemotherapeutic drugs that act by different mechanisms, including vincristine and taxol, which inhibit microtubule formation, cytosine arabinoside, which is an antimetabolite, methotrexate, which is an inhibitor of nucleotide synthesis, etoposide and mitozantron, which inhibit topoisomerase, adriamycin and daunomycin, which intercalate into DNA, cyclophosphamide congeners, which are alkylating agents, and BCNU (a nitrogen mustard), 2-chlorodeoxyadenosine and cisplatin. Thus, expression of a BAP in a cell using the methods described above can reduce the level of free Bcl-2 in a cell and modulate the susceptibility of a cell to apoptosis induced by these or other chemical or physical agents.

The following examples are intended to illustrate but not limit the present invention.

EXAMPLE I

Cloning and Sequence Analysis of Nucleic Acid Molecules Encoding Mouse and Human BAP-1 and Chromosomal Mapping of the Human BAP-1 Gene This example provides a description of the nucleotide sequences encoding mouse and human BAP-1 and the chromosomal location of the human BAP-1 gene.

A sandwich immunoassay was devised for detection of novel Bcl-2-associated proteins produced from bacteriophage lambda-infected *E. coli*. The cDNA expression library used for this cloning procedure represented cDNA that had been derived from a day 11 mouse embryo and cloned into the lambda phage vector, EXlox (library purchased from Novagen, Inc.). *E. coli* strain BL21(DE3)pLysE cells were infected with the bacteriophage lambda-EXlox library and the infected cells were suspended in semi-solid growth medium (0.72% agarose) in 100 mm or 150 mm petri dishes.

Cells were incubated at 37° C. until plaques of 1–2 mm diameter formed. The plaque density was adjusted empirically to yield approximately $1 \times 10^4$ plaques per 100 mm dish or $5 \times 10^4$ plaques per 150 mm dish. Nitrocellulose circles were soaked in 10 mM IPTG, then dried and placed on the surface of the cultures. Incubation was continued at 37° C. for 3 to 16 hrs to induce production of recombinant proteins from the lambda phages. The filters were removed from the dishes, dried to fix the proteins and pre-blocked in a solution containing 75 mM KCl, 20 mM Hepes (pH 7.7), 2.5 mM $MgCl_2$, 2 mM EGTA, 1 mM PMSF, 0.05% Triton X-100, 1 mM dithiothreitol (DTT) and 5% non-fat dried milk powder.

Recombinant Bcl-2 protein was produced in Sf9 insect cells using recombinant bcl-2 DNA-containing baculoviruses as described by Reed et al. (1992). Baculovirus-infected cells were suspended in a buffer containing 1% Triton X-100, 150 mM NaCl, 50 mM Tris (pB 8), 5 mM EDTA and protease inhibitors (protease inhibitors include 1 mM phenylmethylsulfonyl fluoride, 0.23 unit/ml aprotinin, 10 μM leupeptin and 1 mM benzamidine). The resulting suspension contained approximately 200 ug/ml recombinant Bcl-2 protein.

The crude Bcl-2 protein preparation was added to solution A (75 mM KCl, 20 mM Hepes (pH 7.7), 2.5 mM $MgCl_2$, 0.1 mM EGTA, 0.05% Triton X-100, 1 mM PMSF, 1 mM DTT and 1% non-fat dried milk) to achieve a final Bcl-2 protean concentration of approximately 2 μg/ml. Plaque-lifts were incubated overnight with the Bcl-2-containing solution at 4° C. to allow Bcl-2 protein to bind to phage that expressed Bcl-2-binding protein fragments. Following binding, filters were washed 1× at room temperature in solution A, then incubated for 1–2 hrs with 0.1% v/v solution A and ascites fluid from the 4D7 hybridoma, which produces a monoctonal antibody directed against amino acids 61–76 of the human Bcl-2 protein (Reed et al. (1992)). The Bcl-2 antibody complexes were detected on the filters using alkaline phosphatase-conjugated rabbit anti-mouse IgG (Promega; Madison, Wis.). Color development was achieved using nitroblue tetrazolium/bromochloroindoyl phosphate. One positive clone was detected after screening approximately $1 \times 10^6$ plaques.

The positive clone was plaque purified and the cDNA insert was transferred from lambda phage to plasmid using the loxP-cre system. Briefly, BM25.8 cells that contain the Pl-cre recombinase were infected with the lambda bacteriophage and grown in medium containing 50 μg/ml carbenicillin. Plasmid DNA was purified from the resulting antibiotic-resistant colonies of bacteria and both strands were sequenced by the dideoxynucleotide termination method using T7 DNA polymerase.

An 833 bp cDNA was isolated from the plasmid by digestion with EcoRI and Hind III and labelled by a random primer method using $\alpha$-$^{32}$P-dCTP for use as a hybridization probe to obtain overlapping cDNA sequences from a mouse spleen cell cDNA library and a mouse kidney cDNA library. Parts of the 5'-end of the cDNA sequence were derived using the rapid enzymatic amplification of cDNA ends ("RACE") procedure described by Froehman et al., *Proc. Natl. Acad. Sci., USA* 85:8998–9002 (1988), which is incorporated herein by reference. The nucleotide sequence of the mouse BAP-1 DNA is shown in FIG. 1 (SEQ. ID. NO. 1). The nucleotide sequence contains an open reading frame encoding a putative 219 amino acid protein (FIG. 2; SEQ. ID. NO. 2).

The $^{32}$P-labelled 833 bp mouse BAP-1 cDNA also was used as a hybridization probe to screen a human breast cDNA library, which was purchased from Clontech, Inc. Several positive clones were isolated and partially sequenced. The nucleotide sequence of human BAP-1 cDNA clones corresponding to a portion of the coding region of the human BAP-1 protein is shown in FIG. 3 (SEQ. ID. NO. 3). A putative polypeptide derived from the human BAP-1 cDNA is shown in FIG. 4 (SEQ. ID. NO. 4).

The human BAP-1 cDNA sequences were $^{32}$P-labeled and used to screen a cosmid library prepared from human placental genomic DNA (Stratagene; La Jolla, Calif.). Two positive cosmid clones, designated TS131-I and TS131-3, were obtained and used as probes to determine the chromosomal location of the human BAP-1 gene using fluorescence in situ hybridization as described by Inazawa et al., *Genomics* 14:821–822 (1992), which is incorporated herein by reference. The human gene mapped to chromosome 9 at approximately band p13.

EXAMPLE II

Vitro Association of BAP-1 and Bcl-2

This example demonstrates that BAP-1 binds Bcl-2 in vitro.

The 833 bp cDNA sequence that encodes a portion of the mouse BAP-1 protein was subcloned into the pGEX-3X prokaryotic expression plasmid (Pharmacia; Piscataway, N.J.) to produce glutathione-S-transferase (GST)/BAP-1 fusion proteins in *E. coli*. GST-BAP-1 fusion proteins were affinity purified using glutathione-Sepharose (Sigma Chem. Co.; St. Louis, Mo.). As a control, GST protein without BAP-1 sequences was produced and immobilized on glutathione-Sepharose. Following loading of the GST-BAP-1 or GST, the columns were washed with solution A to remove irrelevant proteins.

Bcl-2 protein was produced in Sf9 cells, using a bcl-2 DNA-containing baculovirus as described by Reed et al., 1992), and was added in solution A to the glutathione-Sepharose-immobilized GST/BAP-1 or GST proteins. After incubation at 4° C. for 1 hr, unbound Bcl-2 protein was removed by washing 3× with solution A. The Sepharose particles were collected by centrifugation and boiled in Laemmli sample buffer (62 mM Tris (pH 6.6), 2.3% SDS, 10% glycerol, 5% 2-mercaptoethanol) to release the bound proteins, which were size-fractionated by sodium dodecyl sulfate polyacrylamide gel electrophoresis (SDS-PAGE) using a 10% gel. Following electrophoresis, the proteins were transferred to nitrocellulose filters and incubated with rabbit anti-Bcl-2 antiserum for detection of Bcl-2 protein as described by Reed et al., *Canc. Res.* 51:6529–6538 (1991), which is incorporated herein by reference. As shown in FIG. 6, Bcl-2 protein cosedimented with the GST-BAP-1-Sepharose particles but not with the GST-Sepharose control. No Bcl-2 protein was detected when GST-BAP-1 was incubated with control Sf9 cell lysates, which lack Bcl-2, thus confirming the specificity of the results.

EXAMPLE III

BAP-1 Binds to Bcl-X-L, Bcl-X-S and Bcl-2β

This example demonstrates that BAP-1 binds to various Bcl-2-related proteins in vitro.

BAP-1 protein was examined for binding to the two protein forms encoded by bcl-X gene. The two forms of Bcl-X protein, which are produced by alternative splicing, include a 233 amino acid protein, Bcl-X-L, and a 170 amino acid protein, Bcl-X-S (Boise et al., *Cell* 74:597–608 (1993), which is incorporated herein by reference). Bcl-X-L has 72% homology with Bcl-2 and, like Bcl-2, blocks apoptosis. Bcl-X-S, which lacks a 63 amino acid segment found in Bcl-X-L, also inhibits Bcl-2 function. In addition, the ability of BAP-1 to bind to an alternatively spliced form of Bcl-2, designated Bcl-2β, which lacks the transmembrane domain and diverges in sequence from Bol-2 after amino acid 198, was examined (Tsujimoto and Croce, 1986).

The cDNA sequences encoding Bcl-X-L, Bcl-X-S, Bcl-2 and Bcl-2β were subcloned into plasmid pSK-II (Stratagens), which contains a T7 RNA polymerass binding site. Cloning into pSK-II allows for the in vitro production of RNA, which can be translated in vitro in the presence of $^{35}$S-methionine using reticulocyte lysates to obtain $^{35}$S-labeled proteins. The $^{35}$S-labeled Bcl-2-related proteins (20 µl of in vitro translation mix) were added to approximately 1 µg of GST-BAP-1 fusion protein immobilized on 10 µl of glutathione-Sepharose or with approximately 1 µg of immobilized GST control protein as described above. Following incubation at 4° C. for 1 hr, the Sepharose particles were washed 3× in a solution containing 147 mM KCl, 20 mM Hepes (pH 7.1), 1 mM MgCl$_2$, 0.5 mM EGTA, 1 mM PMSF, 0.05 NP-40, 1 mM DTT, 1% non-fat dried milk and 1% BSA. The Sepharose particles were collected by centrifugation and boiled in Laemmli sample buffer to release any bound $^{35}$S-labeled Bcl-2-related proteins. The released proteins were size-fractionated by SDS-PAGE using a 10% gel and visualized by fluorography using X-ray film.

Bcl-2, Bcl-2-beta, Bcl-X-L and Bcl-X-S protein each bound to the GST-BAP-1 fusion protein but not to GST control protein. These results demonstrate that BAP-1 can bind to a variety of Bcl-2-related proteins.

EXAMPLE IV

Preparation of Anti-BAP-1 Antibodies

This example describes a method for obtaining polyclonal anti-BAP-1 antibodies.

Anti-BAP-1 antibodies were prepared using methods well known in the art (see, for example Harlow and Lane (1988)). Briefly, GST-BAP-1 fusion protein was produced in *E. coli* and affinity purified using glutathione-Sepharose as described above. Approximately 500 ug of purified protein in Freund's complete adjuvant was injected subcutaneously into New Zealand white rabbits. The original immunization was followed by three weekly booster immunizations using 500 ug of GST/BAP-1 protein in Freund's incomplete adjuvant. Following the third booster dose, immunizations were administered at 4–6 week intervals; blood samples were collected 1 to 2 weeks after each booster for preparation of sera.

Antibodies that reacted with the GeT protein were removed by passing a 1:10 (v:v) solution of rabbit antiserum in phosphate buffer saline (PBS) through a column containing GST protein immobilized on glutathione Sepharose as described in Example II, above. The effluent was passed through a second column containing GST/BAP-1-Sepharose and specific antibodies were eluted using 0.2M glycine 2.2). The sample pH was adjusted to pH 7.4 and dialyzed against PBS containing 0.2% NaN3. The anti-BAP-1 antibodies were used for immunoblotting, immunoprecipitation and immunocytochemistry experiments as described below (see, also, Hanada et al., *Canc. Res.* 53:4978–4986 (1993); Reed et al. (1991); Louie et al., *Amer. J. Pathol.* 139:1231–1237 (1991), each of which is incorporated herein by reference.

Antisera also were raised to a synthetic peptide representing the last 19 amino acids at the carboxy terminus of the mouse BAP-1 protein (see FIG. 2). The peptide was synthesized to contain at its amino terminus a cystsine residue, which was used to covalently conjugate the peptide to a carrier protein, maleimide-activated KLH, as described by Reed et al. (1991). The KLH-peptide conjugates were used to immunize rabbits as described above.

Standard immunoblot and immunoprecipitation assays were performed as described by Reed et al. (1991) using the antisera prepared as described above. The antisera detected a protein having an apparent molecular weight of approximately 30 kiloDaltons (kDa), which is somewhat larger than the molecular weight of 24,846 Da predicted from the 219 amino acid open reading frame present in the mouse BAP-1 cDNA (FIG. 1). This discrepancy likely is due to the highly acidic nature of the BAP-1 protein (14% glutamic acid), which can result in aberrant migration in SDS-containing polyacrylamide gels. The aberrant mobility of the BAP-1 protein was confirmed by electrophoresis of a protein prepared by in vitro transcription and translation of a cDNA that lacks the 5'-untranslated region and contains only the open reading frame coding for the 219 amino acid polypeptide.

Immunoblot analysis of BAP-1 in various tissue samples and immunocytochemical detection of BAP-1 protein in formalin-fixed, paraffin-embedded tissue-sections indicate that the protein is present in a wide variety of tissues. BAP-1 is most abundant in thymus, spleen and lymph nodes, moderately abundant in brain, and minimally detectable in kidney, skeletal muscle and liver.

EXAMPLE V

BAP-1 and Bcl-2 Associate In Vivo

This example demonstrates that BAP-1 and Bcl-2 form a bound complex in vivo.

Anti-BAP-1 antibodies were used to show that Bcl-2 protein co-immunoprecipitates with BAP-1. A murine cell line, 32D, was transfected with either a bcl-2 expression plasmid, pZip-bcl-2, which produces the human Bcl-2 protein, or with a negative control plasmid, pZip-neo. The cell lines were designated 32D-BCL-2 and 32D-NEO, respectively (see Baffy et al., *J. Biol. Chem.* 268:6511–6519 (1993); Tanaka et al., *J. Biol. Chem.* 268:10920–10926 (1993), each of which is incorporated herein by reference).

32D cells were lysed in a lysis buffer containing 147 mM KCl, 20 mM Tris (pH 7.5), 2.5 mM $MgCl_2$, 0.05 mM EGTA, 0.5% NP-40 and protease inhibitors. Approximately 500 µg of the resulting proteins were incubated with 5 µl of anti-BAP-1 antiserum for 2 hr at 4° C. Following incubation, the immune complexes were added to 25 µl of protein A-Sepharose. The sample was washed 3× with the lysis buffer and the Sepharose particles were pelleted by centrifugation and boiled in Laemmli sample buffer. The proteins were size-fractionated by SDS-PAGE and transferred to nitrocellulose filters. The filters were incubated with 5–10 ml phosphate buffered saline (pH 7.4) containing 2% (w/v) BSA and 0.1% (v/v) of a rabbit antiserum specific for the human Bcl-2 protein, then with horseradish peroxidase-conjugated goat-anti-rabbit IgG and the Lumiphos® substrate (Boehringer Mannheim, Inc.) as suggested by the supplier. Chemiluminescence was detected by autoradiography.

A 26 kDa protein corresponding to the human Bcl-2 protein was detected in lysates derived from 32D-BCL-2 cells, which produce the human Bcl-2 protein, but not in lysates prepared from 32D-NEO cells, which lack human Bcl-2 protein. These results indicate that Bol-2 and BAP-1 associate in cells in vivo.

EXAMPLE VI

The Raf-1 Kinase Associates with Bcl-2 in vivo

This example demonstrates that a Raf-related protein, the Raf-1 kinase, has the characteristics of a Bcl-2-associated protein.

To facilitate detection of the Raf-1 kinase interaction with Bcl-2, an expression plasmid, pEc12 (Heidecker et al. (1990), which produces an amino-terminal truncated, constitutively active 35 kDa form of the Raf-1 kinase, was introduced in either 32D-BCL-2 cells or 32D-NEO cells, as described above. Production of the 35 kDa Raf-1 kinase was confirmed by immunoblot analysis using a polyclonal antiserum raised against a synthetic peptide corresponding to the carboxy-terminal 16 amino acids of Raf-1 as described by Reed et al., *Cell Growth Diff.* 2:235–243 (1991b), which is incorporated herein by reference.

Ten million of each of the resulting 32D-BCL-2/Raf cells and 32D-NEO/Raf cells were lysed in a solution containing 147 mM KCl, 20 mM Tris (pH 7.5), 2.5 mM $MgCl_2$, 0.05 mM EGTA, 0.5% NP-40 and protease inhibitors. Bcl-2 protein was immunoprecipitated using 2.5 µl of anti-Bcl-2 polyclonal antiserum and 25 µl of protein A-Sepharose. The samples were washed 3× with lysis solution and boiled in Laemmli sample buffer. Proteins were size-fractionated by SDS-PAGE (10% gel) and transferred to nitrocellulose filters. The resulting blots were incubated with 0.1% (v/v) of the Raf-1-specific antiserum in 5 to 10 ml of phosphate buffered saline containing 2% BSA. Bound antibodies were detected using biotinylated goat anti-rabbit IgG (Vector Labs, Inc.) and an avidin-biotin complex reagent containing horseradish peroxidase (Vector Labs, Inc.), followed by diaminobenzidine for color detection essentially as described by Hanada et al. (1993).

A 35 kDa band corresponding to the truncated Raf-1 kinase was detected by this immunoblot analysis of Bcl-2-containing immune complexes prepared from 32D-BCL-2/Raf cells. No band was observed in the lane corresponding to lysate prepared from 32D-NEO/Raf cells, reflecting that these cells do not express human Bcl-2 and that the anti-Bcl-2 antibody is specific for human Bcl-2 (Reed et al. (1991). These results indicate that the truncated 35 kDa form of Raf-1 can associate with Bcl-2 in vivo.

The ability of the full length Raf-1 kinase to bind Bcl-2 also was examined. Instead of immunoblot analysis, a more sensitive in vitro immune complex kinase assay was used (Reed et al., 1991b). Lysates were prepared from 32D-BCL-2 cells, which overexpress human Bcl-2 protein and express endogenous Raf-1 kinase. Immunoprecipitation assays were performed using either an anti-Bcl-2 monoclonal antibody, 4D7 (Reed et al. (1992), or an isotype and subclass-matched control mouse $IgG_1$ monoclonal antibody (Sigma Chem. Co.). Immune complexes were washed and resuspended in a kinase reaction buffer containing $\gamma$-$^{35}$P-ATP and a peptide substrate exactly as described by Reed et al. (1991b). Following incubation for 20 min at 30° C., the peptide substrate was separated from unincorporated $\gamma$-$^{32}$P-ATP by SDS-PAGE using a 20% gel and the relative amount of incorporated $^{32}$P was determined by autoradiography.

Immune complexes prepared using the Bcl-2-specific monoclonal antibody contained 20× to 50× more Raf-1 kinase activity than control immune complexes. This result indicates that the full length endogenous Raf-1 kinase can associate with protein complexes containing Bcl-2 protein.

EXAMPLE VII

Drug Screening Assay

This example describes an assay useful for screening for agents such as drugs that alter the affinity of binding of BAP-1 with Bcl-2.

FIG. 7 presents a scheme for using a BAP such as the BAP-1 protein or the Raf-1 kinase in a drug screening assay that is suitable for automated high through-put random drug screening. A cDNA encoding BAP-1 was subcloned into either the pGEX-3X plasmid, which produces GST-BAP-1 fusion proteins in E. coli, as described above, or into a baculovirus transfer vector, pAcSG-His, which produces histidine-tagged fusion proteins in Sf9 insect cells (PharMingen, Inc.). The proteins were affinity purified by standard methods using either glutathione-Sepharose, as described above, or nickel-chelation chromatography, essentially as described by Smith and Johnson, Gene 67:31–40 (1988), which is incorporated herein by reference. The specific recombinant fusion proteins were eluted using excess glutathione in PBS (pH 7.4) or in imidazole (pH 6.0), respectively. Following dialysis, the GST-BAP-1 and His-BAP-1 fusion proteins were immobilized to solid supports taking advantage of the ability of the GST protein to specifically bind glutathione and of the histidine-6 peptide region to chelate nickel (Ni) ion.

The assay can utilize any Bcl-2-related protein, including a truncated form of the Bcl-2 protein that lacks the hydrophobic transmembrane domain, which obviates problems of solubility. The truncated protein was engineered to contain a mutation of Cys→Ala at amino acid position 158 of the human Bcl-2 protein. As a result of this mutation, the protein contained only one cysteine residue and, therefore, has a free sulfhydryl (SH) group available for chemical modification. The 158 Cys→Ala mutation does not impair the biological activity of the Bcl-2 protein when expressed in mammalian cells. These results indicate that the mutant Bcl-2 protein folds correctly and retains its ability to interact with relevant proteins in cells.

Since the mutant Bcl-2 protein has a single free sulfhydryl group located at its carboxy terminus, several different chemical modifications can be used to attach a detectable moiety such as a fluorescent molecule, a radiolabel or another protein, which can be detected using a specific antibody or other specific reagent. For example, fluorescein-5 maleimide can be attached as a fluorescent tag for the Bcl-2 protein. Various agents such as drugs are screened for the ability to alter the association of Bcl-2 and BAP-1. The agent, BAP-1 and fluorescent-Bcl-2 can be added together, incubated for 30 min to allow binding, then washed to remove unbound fluorescent-Bcl-2 protein. The relative amount of binding of fluorescent-Bcl-2 protein in the absence as compared to the presence of the agent being screened is determined by detecting the relative light emission of the fluorochrome.

The assay is readily adapted for examining the interaction of a BAP with other Bcl-2-related proteins such as Bcl-X-L, Bcl-X-S, Mcl-1, BHRF-1 or A1, as described above, and other Bcl-2-related proteins such as Bax (Oltari et al., Cell 74:609–619 (1993), which is incorporated herein by reference) or LMH-5W (Neilan et al., J. Virol. 67:4391–4394 (1993), which is incorporated herein by reference). The screening assay is useful for detecting agents that alter the association of a BAP and a Bcl-2-related protein by increasing or decreasing their binding affinity.

In addition, the drug screening assay is readily adaptable for identifying the effect of an agent on the binding of other BAPproteins such as the Raf-1 kinase with a Bcl-2-related protein. In this case, it can be advantageous to include in the assay a third protein such as a member of the Ras family of proteins, which are known to interact with the Raf kinase (Vojtek et al., Cell. 74:205–214 (1993), which is incorporated herein by reference). The addition of the Ras protein can facilitate the interaction of Raf-1 with a Bcl-2-related protein in vitro and will result in an assay that more closely mimics the interactions that occur in the intracellular environment.

Although the invention has been described with reference to the examples above, it should be understood that various modifications can be made without departing from the spirit of the invention. Accordingly, the invention is limited only by the following claims.

We claim:

1. A nucleic acid molecule having a nucleotide sequence selected from the group consisting of SEQ ID NO: 1 and SEQ ID NO: 3.

2. A nucleotide sequence complementary to a nucleotide sequence selected from the group consisting of SEQ ID NO: 1 and SEQ ID NO: 3.

* * * * *

UNITED STATES PATENT AND TRADEMARK OFFICE
CERTIFICATE OF CORRECTION

PATENT NO. : 5,686,595
DATED : Nov. 11, 1997
INVENTOR(S) : Reed et al.

Page 1 of 3

It is certified that error appears in the above-identified patent and that said Letters Patent is hereby corrected as shown below:

In the Title Page, column 1, line [62], please delete "152,405" and replace therefor with --152,485--.

In column 1, line 4, please delete "Nov. 11," and replace therefor with --Nov. 12,--.

In column 4, line 2, please delete "due a" and replace therefor with --due to a--.

In column 6, line 35, please delete "anti-HAP-1" and replace therefor with --anti-BAP-1--.

In column 6, line 36, please delete "HAP-1" and replace therefor with --BAP-1--.

In column 6, line 56, please delete "such" and replace therefor with --such as--.

In column 9, line 30, please delete "hematcpoietic" and replace therefor with --hematopoietic--.

In column 12, line 29, please delete "protean" and replace therefor with --protein--.

In column 12, lines 36-37, please delete "monoc-tonal" and replace therefor with --monoc-lonal--.

UNITED STATES PATENT AND TRADEMARK OFFICE
CERTIFICATE OF CORRECTION

PATENT NO. : 5,686,595
DATED : Nov. 11, 1997
INVENTOR(S) : Reed et al.

It is certified that error appears in the above-identified patent and that said Letters Patent is hereby corrected as shown below:

In column 13, line 13, please delete "TS131-I" and replace therefor with --TS131-1--.

In column 13, line 22, please delete "Vitro" and replace therefor with --In Vitro--.

In column 14, line 9, please delete "Bol-2" and replace therefor with --Bcl-2--.

In column 14, line 13, please delete "(Stragens)" and replace therefor with --(Stratagene)--.

In column 14, line 13, please delete "polymerass" and replace therefor with --polymerase--.

In column 14, line 54, please delete "GeT" and replace therefor with --GST--.

UNITED STATES PATENT AND TRADEMARK OFFICE
CERTIFICATE OF CORRECTION

PATENT NO. : 5,686,595
DATED : Nov. 11, 1997
INVENTOR(S) : Reed et al.

It is certified that error appears in the above-identified patent and that said Letters Patent is hereby corrected as shown below:

In column 14, line 60, please delete "2.2" and replace therefor with --(pH 2.2)--.

In column 16, line 2, please delete "Bol-2" and replace therefor with --Bcl-2--.

Signed and Sealed this

Tenth Day of April, 2001

Attest:

NICHOLAS P. GODICI

Attesting Officer

Acting Director of the United States Patent and Trademark Office